United States Patent
Gordon et al.

(10) Patent No.: US 10,017,816 B2
(45) Date of Patent: Jul. 10, 2018

(54) METHODS AND COMPOSITIONS FOR SEQUENCING NUCLEIC ACIDS USING CHARGE

(71) Applicant: Intelligent Bio-Systems, Inc., Waltham, MA (US)

(72) Inventors: Steven Gordon, Weston, MA (US); Jerzy Olejnik, Brookline, MA (US)

(73) Assignee: INTELLIGENT BIO-SYSTEMS, INC., Waltham, MA (US)

( * ) Notice: Subject to any disclaimer, the term of this patent is extended or adjusted under 35 U.S.C. 154(b) by 0 days.

(21) Appl. No.: 15/095,560

(22) Filed: Apr. 11, 2016

(65) Prior Publication Data

US 2016/0222446 A1   Aug. 4, 2016

Related U.S. Application Data

(62) Division of application No. 13/212,910, filed on Aug. 18, 2011, now Pat. No. 9,309,569.

(60) Provisional application No. 61/377,153, filed on Aug. 26, 2010.

(51) Int. Cl.
  *C12Q 1/6874* (2018.01)
  *C12Q 1/6869* (2018.01)

(52) U.S. Cl.
  CPC ........ *C12Q 1/6874* (2013.01); *C12Q 1/6869* (2013.01)

(58) Field of Classification Search
  None
  See application file for complete search history.

(56) References Cited

U.S. PATENT DOCUMENTS

2007/0117102 A1* 5/2007 Buzby .................... C07H 21/04
                                                 435/6.12
2009/0181381 A1* 7/2009 Oldham ............... C12Q 1/6825
                                                 435/6.11

* cited by examiner

*Primary Examiner* — Joseph G. Dauner
(74) *Attorney, Agent, or Firm* — Medlen & Carroll, LLP

(57) ABSTRACT

The invention relates to methods and compositions, and systems for determining the identity of nucleic acids in nucleotide sequences, and in particular, sequences that contain consecutive repeats of a particular base. For example, a consecutive repeat of a particular base may be identified by a charged ion detection (e.g., hydrogen ion detection).

12 Claims, 3 Drawing Sheets

X = O, NH; $R_1, R_2, R_3, R_4$ = H, alkyl group

X = O, NH; $R_1, R_2$ = H, alkyl group

X = O, NH; $R_1, R_2, R_3, R_4$ = H, alkyl group

X = O, NH; $R_1, R_2$ = H, alkyl group

METHODS AND COMPOSITIONS FOR SEQUENCING NUCLEIC ACIDS USING CHARGE

FIELD OF THE INVENTION

The invention relates to methods and compositions, and systems for determining the identity of nucleic acids in nucleotide sequences, and in particular, sequences that contain consecutive repeats of a particular base.

BACKGROUND OF THE INVENTION

Over the past 30 years, the amount of DNA sequence information that has been generated and deposited into Genbank has grown exponentially. Many of the next-generation sequencing technologies use a form of sequencing by synthesis (SBS), wherein specially designed nucleotides and DNA polymerases are used to read the sequence of single-stranded DNA templates in a controlled manner. Pyrosequencing is a form of SBS which allows sequencing of a single strand of DNA by synthesizing the complementary strand along it, one base pair at a time, and detecting which base was actually added at each step.

Rotherberg et al. teach the use of large arrays of chemically sensitive FETs (chemFETs) or more specifically ISFETs for monitoring reactions, including for example nucleic acid (e.g., DNA) sequencing reactions, based on monitoring analytes present, generated or used during a reaction. See U.S. Patent Application Publication No. 20100137143, hereby incorporated by reference. More generally, arrays including large arrays of chemFETs may be employed to detect and measure static and/or dynamic amounts or concentrations of a variety of analytes (e.g., hydrogen ions, other ions, non-ionic molecules or compounds, etc.). Rotherberg et al. teach the measurement of hydrogen ions, rather than the pyrophosphate normally measured in pyrosequencing.

However, there are types of sequences which are difficult to sequence (even with these newer approaches), and in particular, sequences that contain consecutive repeats of a particular base. What is needed is an improved method which addresses the ability to sequence all types of sequence.

SUMMARY OF THE INVENTION

DNA sequences often have so-called homopolymeric regions (e.g. T-T-T-T-T). Pyrosequencing of DNA template containing the homopolymeric regions produces results which make it very difficult to identify the exact sequence from the data (e.g. is the region T-T-T-T or T-T-T-T-T?) because pyrosequencing is done with unblocked nucleotides and relies on the magnitude of the signal to determine the number of incorporations for the homopolymeric region. This becomes a very large problem as read lengths increase because secondary effects such as non-specific binding reactions and synthesis dephasing are cumulative with the number of incorporation reaction cycles. These effects contribute to the measurement noise and make it more difficult to use a single detector intensity value as an accurate indicator of the number of incorporations in a homopolymeric region. It is also a problem where the sequence contains multiple regions of this type.

The invention relates to methods and compositions, and systems for determining the identity of nucleic acids in nucleotide sequences, and in particular, sequences that contain one or more consecutive repeats of a particular base (so-called homopolymeric regions). In one embodiment, method for sequencing nucleic acids comprising, a) incorporating one or more nucleotides into a plurality of nucleic acids in one or more reaction chambers in contact with one or more ion detectors, wherein said nucleotides comprise a 3'-OH blocking group, said blocking group preventing any further nucleotide incorporation and any further extension of the nucleic acids in which the nucleotide is incorporated unless removed, and b) detecting hydrogen ions released upon nucleotide incorporation by said one or more ion detectors. In one embodiment, said blocking group is a removable chemical moiety. It is not intended that the present invention be limited by the nature of the blocking group. In one embodiment, said removable chemical moiety comprises a disulfide bond. In one embodiment, said removable chemical moiety comprises an azido group. In one embodiment, said removable chemical moiety comprises an azidomethyl ether. In one embodiment, said removable chemical moiety comprises an aminoxy group. In one embodiment, said removable chemical moiety comprises an oxime group. It is also not intended that the present invention be limited to a particular type of sequence with a particular homopolymer region. In one embodiment, a portion of the sequence of said nucleic acid comprises consecutive identical bases of the formula $X_n$, where X is any base and n is a whole number between 3 (e.g. A-A-A, G-G-G, C-C-C, etc.) and 10. In one embodiment, the nucleic acid to be sequenced is immobilized (e.g. on a bead, in a well, etc.) For example, one may immobilize template DNA on a solid surface by its 5' end. Incorporation of the nucleotides typically takes place in a primer which becomes a complementary extension strand of the strand being sequenced. One may accomplish this by annealing a sequencing primer to the nucleic acid (e.g. to a consensus sequence that has been introduced into the nucleic acid to be sequence) and introducing a DNA polymerase (including non-natural polymerases which have been mutated to improve performance, including incorporation of nucleotide analogs with bulky groups).

While the above-described embodiment utilizes the charge coming from the 3'-OH group of an already incorporated nucleotide in the chain (i.e. resulting from the loss of H when the new nucleotide is incorporated), the present invention also contemplates embodiments, where the charge comes from chemical groups designed into the nucleotide. Such embodiments allow for leaving groups or cleavable groups with larger (more easily detectable) charges, including both positive and negative charges. Thus, in another embodiment, the present invention contemplates a method for sequencing nucleic acids comprising, a) incorporating one or more nucleotides into a plurality of nucleic acids in one or more reaction chambers in contact with one or more charge detectors (including ion detectors), wherein said nucleotides comprise a cleavable moiety (or label) and a 3'-OH blocking group, said blocking group preventing any further nucleotide incorporation and any further extension of the nucleic acids in which the nucleotide is incorporated unless removed, b) cleaving said cleavable moiety (or label) under conditions such that a charged moiety is produced, and c) detecting said charged moiety with said one or more charge detectors. In one embodiment, said charged moiety is positively charged. In another embodiment, said charged moiety is negatively charged. Indeed, one type of nucleotide (e.g. T) might have a group that can be cleaved so as to produce a positive charge, while another type of nucleotide (e.g. G) might have a group that can be cleaved so as to produce a negative charge (thereby allowing for the nature of the charge to correlate with the nature/identity of the base). In yet another embodiment, said charged moiety may have a different magnitude for each type of nucleotide. For example, one type of nucleotide (e.g. T) might have one level of positive charge, while another nucleotide (e.g. A) might have two (or three, or four, etc.) times that level of positive charge. These embodiments could be combined such that pyrimidines (C, T, U) have a positive charge, but differ in magnitude, while purines (A and G) have a negative charge, but differ in magnitude. On the other hand, the pyrimidines could have the negative charge, but differ in magnitude, which the purines could have the positive charge, but differ in magnitude. In either case, charge and magnitude of charge would permit identification of the incorporated base.

In one embodiment, there is a wash step prior to step b) which removes unincorporated nucleotides (and any other reagent). It is sufficient that this wash steps remove the majority of excess reagents (and more preferably 90% of such reagents), even if not removing %100. It is not intended that the present invention be limited by the nature of the agent used to cleave the moiety or label. In one embodiment, said label is cleaved enzymatically. In one embodiment, said label is cleaved chemically. It is also not intended that the present invention be limited to a particular type of sequence with a particular homopolymer region. In one embodiment, the present invention contemplates a portion of the sequence of said nucleic acid comprises consecutive identical bases of the formula $X_n$, where X is any base and n is a whole number between 3 and 10. In one embodiment, the cleavable label is attached through a cleavable linker to the base of said nucleotide.

DEFINITIONS

To facilitate understanding of the invention, a number of terms are defined below, and others are found elsewhere in the specification.

The term "plurality" means two or more.

The term "nucleotide sequence" refers to a polymer comprising deoxyribonucleotides (in DNA) or ribonucleotides (in RNA). Nucleotides have a base selected from the group of adenine (A), guanine (G), cytosine (C), thymine (T), and uracil (U).

The term "interrogation position" when made in reference to a nucleotide sequence refers to a location of interest in the sequence, such as the location at which the identity of a nucleic acid is sought to be determined.

The terms "cleavable moiety," "cleavable marker," and "cleavable label" are interchangeably used to describe a chemical moiety that, when attached to a composition of interest (e.g. to the base of a nucleotide), acts as a marker for the presence of the composition of interest. The "label" need not be detectable visually (although such embodiments are also contemplated since some dyes have charge). The label is preferably detected by charge (e.g. after cleavage). The present invention envisions labels that would carry a net negative or positive charge. For example, one can use mono, di and tricarboxylic acids (acetic, oxalic, malonic, succinic, citric etc., since they will be deprotonated) attached via a cleavable linker for negative charge (e.g. the cleavable linker attached to the base or another part of the nucleotide). Or one could use mono, di or triamines (since they will be protonated) for positive charge. Finally, one can use labels that would release protons upon cleavage.

The invention's compositions and methods contemplate using modified nucleotides. The terms "nucleotide" and "nucleic acid" refer to constituents of nucleic acids (DNA and RNA) that contain a purine or pyrimide base, such as adenine (A), guanine (G), cytosine (C), uracil (U), or thymine (T)), covalently linked to a sugar, such as D-ribose (in RNA) or D-2-deoxyribose (in DNA), with the addition of from one to three phosphate groups that are linked in series to each other and linked to the sugar. The term "nucleotide" includes native nucleotides and modified nucleotides.

"Native nucleotide" refers to a nucleotide occurring in nature, such as in the DNA and RNA of cells. In contrast, "modified nucleotide" refers to a nucleotide that has been modified by man, such as using chemical and/or molecular biological techniques compared to the native nucleotide. The terms also include nucleotide analogs attached to one or more probes to facilitate the determination of the incorporation of the corresponding nucleotide into the nucleotide sequence. In one embodiment, nucleotide analogues are synthesized by linking a unique label through a cleavable linker to the nucleotide base or an analogue of the nucleotide base, such as to the 5-position of the pyrimidines (T, C and U) and to the 7-position of the purines (G and A), to use a small cleavable chemical moiety to cap the 3'-OH group of the deoxyribose or ribose to make it nonreactive, and to incorporate the nucleotide analogues into the growing nucleotide sequence strand as terminators, such as reversible terminators and irreversible terminators. Detection of the unique label (e.g. by charge) will yield the sequence identity of the nucleotide. Upon removing the label and the 3'-OH capping group, the polymerase reaction will proceed to incorporate the next nucleotide analogue and detect the next base. Other nucleotide analogs that contain markers, particularly cleavable markers, are also contemplated, such as those configured using allyl groups, azido groups, and the like, and which are further described below.

GENERAL DESCRIPTION OF THE INVENTION

Figure 1:
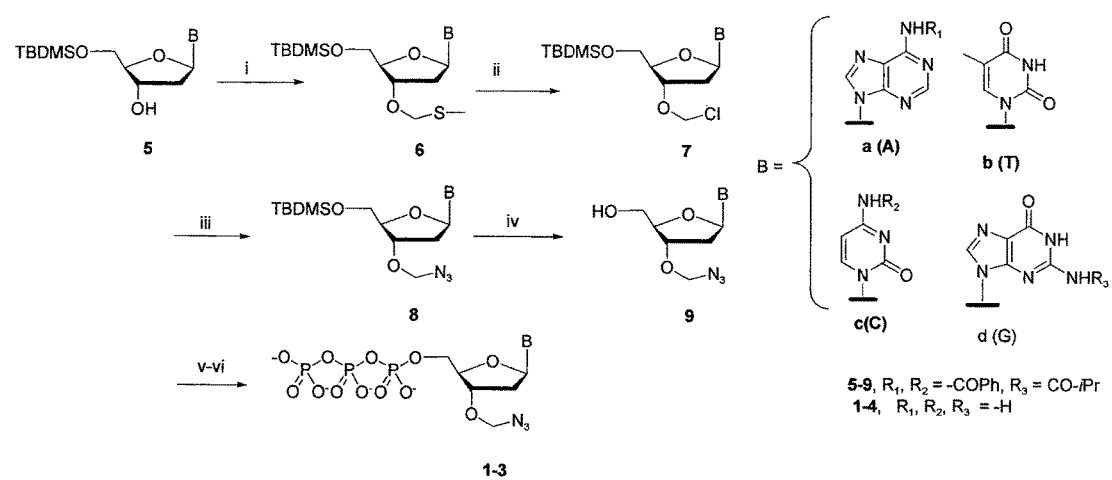
FIG. 1 shows synthesis of 3'-O-azidomethyl-dNTPs where the steps denote treatment with (i) DMSO, AcOH, $Ac_2O$, 48 h; (ii) $SO_2Cl_2$, dry $CH_2Cl_2$, 1-2 h; (iii) $NaN_3$ in DMF, 3 h; (iv) $NH_4F$ in MeOH, 16-20 h; (v) $(MeO)_3PO$, $POCl_3$ then $(t-Bu_3NH)_4P_2O_7$, TEAB, 1 h; vi) $NH_4OH$.

The present invention, in one embodiment, contemplates using the blocked nucleotides described herein together with large scale FET arrays for measuring one or more analytes (e.g. ions and charged moieties). In the various embodiments disclosed herein, FET arrays include multiple "chemFETs," or chemically-sensitive field-effect transistors, that act as chemical sensors. An ISFET is a particular type of chemFET that is configured for ion detection, and ISFETs may be employed in various embodiments disclosed herein. Other types of chemFETs contemplated by the present disclosure include ENFETs, which are configured for sensing of specific enzymes. It should be appreciated, however, that the present disclosure is not limited to ISFETs and ENFETs, but more generally relates to any FET that is configured for some type of chemical sensitivity.

According to yet other embodiments, the present disclosure is directed generally to inventive methods and apparatus relating to the delivery to the above-described large scale chemFET arrays of appropriate chemical samples to evoke corresponding responses. The chemical samples may comprise (liquid) analyte samples in small reaction volumes, to facilitate high speed, high-density determination of chemical (e.g., ion or other constituent) concentration or other measurements on the analyte.

For example, some embodiments are directed to a "very large scale" two-dimensional chemFET sensor array (e.g., greater than 256 k sensors), in which one or more chemFET-containing elements or "pixels" constituting the sensors of such an array are configured to monitor one or more independent chemical reactions or events occurring in proximity to the pixels of the array. In some exemplary implementations, the array may be coupled to one or more microfluidics structures that form one or more reaction chambers, or "wells" or "microwells," over individual sensors or groups of sensors of the array, and apparatus which delivers analyte samples to the wells and removes them from the wells between measurements. Even when microwells are not employed, the sensor array may be coupled to one or more microfluidics structures for the delivery of one or more analytes to the pixels and for removal of analyte(s) between measurements.

In various embodiments, an analyte of particular interest is hydrogen ions, and large scale ISFET arrays according to the present disclosure are specifically configured to measure pH. In other embodiments, chemFET arrays may be specifically configured to measure pH or one or more other analytes that provide relevant information relating to a particular chemical process of interest. In various aspects, the chemFET arrays are fabricated using conventional CMOS processing technologies, and are particularly configured to facilitate the rapid acquisition of data from the entire array (scanning all of the pixels to obtain corresponding pixel output signals). See U.S. Patent Application Publication No. 20090026082, hereby incorporated by reference.

DESCRIPTION OF PREFERRED EMBODIMENTS

In one embodiment, the nucleotide analogs are exemplified by nucleotide compositions comprising compounds of the following general structure:

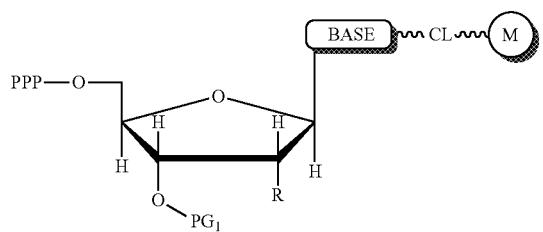

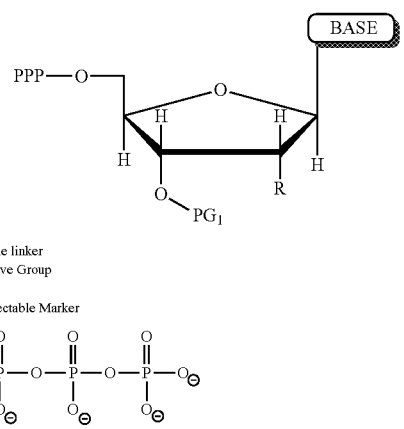

CL = Cleavable linker
PG₁ = Protective Group

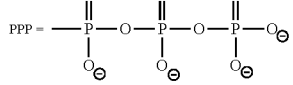 = Detectable Marker $$PPP = -\overset{O}{\underset{O_\ominus}{\overset{\|}{P}}}-O-\overset{O}{\underset{O_\ominus}{\overset{\|}{P}}}-O-\overset{O}{\underset{O_\ominus}{\overset{\|}{P}}}-O_\ominus$$

Where PG1 stands for protective group that is selectively removable and, and CL stands for cleavable linker, which is also selectively cleavable, and R is selected from the group of H, OH, F, $NH_2$. Several particular embodiments of this invention are contemplated. In one embodiment these nucleotide compositions can be incorporated into the nucleic acid by nucleic acids modifying enzymes in a controlled fashion to decode the identity of the bases encoded by the marker moiety M. Once the marker moiety has been cleaved off, identity of the base may be decoded by measuring the change in charge in the reaction chamber due to the released marker moieties. In one embodiment, this invention contemplates the use of the cleavable linkers based on the "trimethyl lock" mechanism or the "1,6-rearrangement" mechanism. The 3'-O-protective groups which act as reversible terminators can also be cleaved off to enable addition of the next nucleotide. This invention contemplates the use of azidomethyl, methylaminoxy, disulfide, aminoxy, oxime and allyl groups as reversible 3'-OH terminators.

Figure 2:
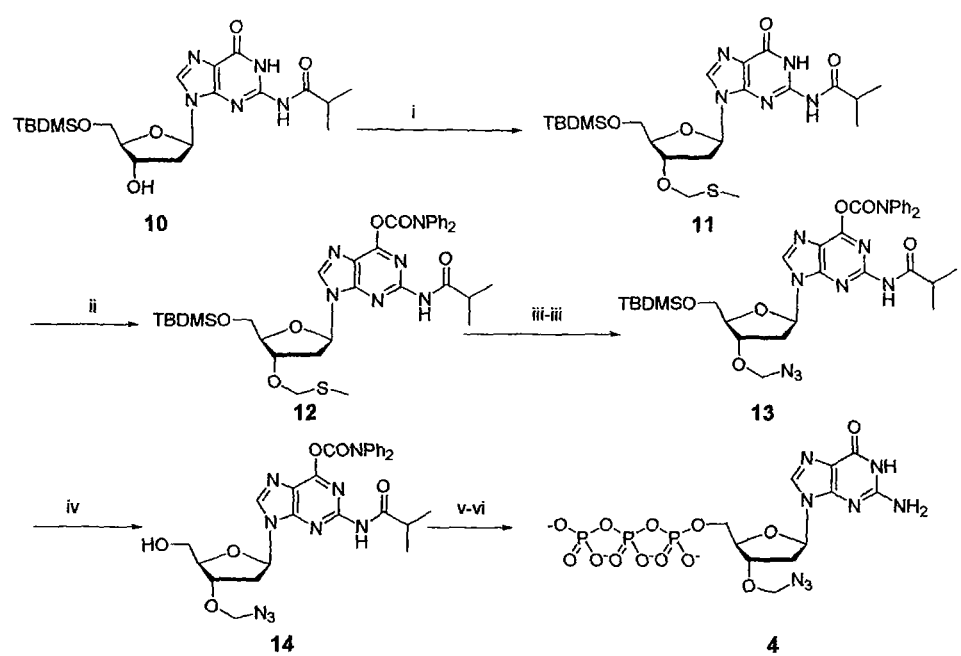
FIG. 2 shows synthesis of 3'-O-azidomethyl-dGTP where the steps denote treatment with (i) DMSO, AcOH, $Ac_2O$, 48 h; (ii) $Ph_2NCOCl$, DIEA, Pyridine 3 h; (iii) $SO_2Cl_2$, dry $CH_2Cl_2$, 1-2 h; (iii) $NaN_3$ in DMF, 3 h; (iv) $NH_4F$ in MeOH, 24 h; (v) $(MeO)_3PO$, $POCl_3$ then $(t-Bu_3NH)_3P_2O_7H$, TEAB, 1 h; (vi) $NH_4OH$.

Methods for synthesizing exemplary nucleotide analogs that contain cleavable markers configured using azido groups are shown in FIGS. 1 and 2.

The invention contemplates the use of the cleavable linkers based on the "trimethyl lock" mechanism or the "1,6-rearrangement" mechanism. The 3'-O-protective groups which act as reversible terminators can also be cleaved off to enable addition of the next nucleotide. The invention contemplates the use of azidomethyl, aminooxy, methylaminoxy and allyl groups as reversible 3'-OH terminators.

A. Cleavable Linkers (Cl)

Cleavable linkers are exemplified by trimethyl lock based linkers and 1,6-rearrangement linkers as further described below.

1. Trimethyl Lock Based Linkers

Cleavable linkers are the linkers linking the marker molecule M to the base and these can be selectively cleaved using specific cleaving agents. Specifically, this invention contemplates the use of a "trimethyl lock" structure as the cleavage mechanism. These structures are well known in the chemical arts and have been used before in controlled drug release applications. The general structures of cleavable trimethyl lock based linker utilized in particular embodiments of the present invention are shown below:

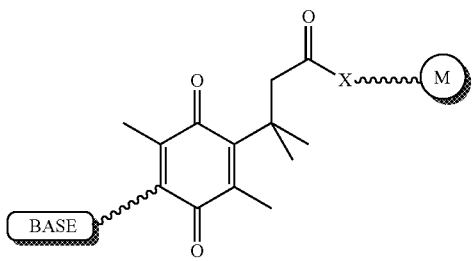

The above shows exemplary embodiment A where BASE is selected from any ribo- or deoxyribo-nucleobases: adenosine, cytidine, guanosine, thymidine and analogs, M is a detectable marker, and X is a divalent group selected from NH, O, S.

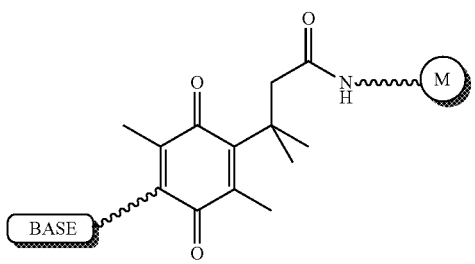

The above shows exemplary embodiment B where BASE is selected from any ribo- or deoxyribo-nucleobases: adenosine, cytidine, guanosine, thymidine and analogs, M is a detectable marker, and X is NH.

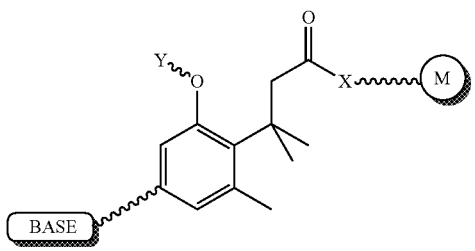

The above shows exemplary embodiment C where BASE is selected from any ribo- or deoxyribo-nucleobases: adenosine, cytidine, guanosine, thymidine and analogs, M is a detectable marker, and X is a divalent group selected from NH, O, S, and Y is a selectively removable protective group.

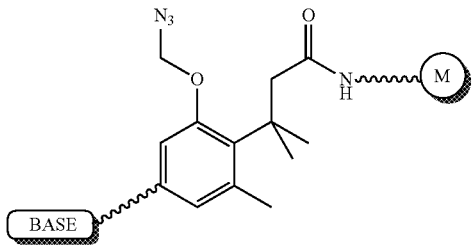

The above shows exemplary embodiment D where BASE is selected from any ribo- or deoxyribo-nucleobases: adenosine, cytidine, guanosine, thymidine and analogs, M is a detectable marker, X is NH, and Y is an azidomethyl group.

The linkers in the present invention leverage the ability of the trimethyl lock system to create cleavably linked nucleotides.

2. 1,6-Rearrangement Linkers

The invention contemplates another category of cleavable linkers linking the detectable marker moiety to the nucleotide that are based on 1,6 quinone methide rearrangement mechanism (Carl et al. (1981). J. Med. Chem. 24(5):479-480; Duimstra et al. (2005). J. Am. Chem. Soc. 127(37): 12847-12855). These structures are well known in the chemical arts and they have been used before for the controlled drug release applications and for chemical synthesis (Azoulay et al. (2006) Bioorganic & Medicinal Chemistry Letters 16(12): 3147-3149; Murata et al. (2006) Tetrahedron Letters 47(13): 2147-2150). The general structures of cleavable 1,6 rearrangement mechanism based linker utilized in some embodiments of the present invention are shown below:

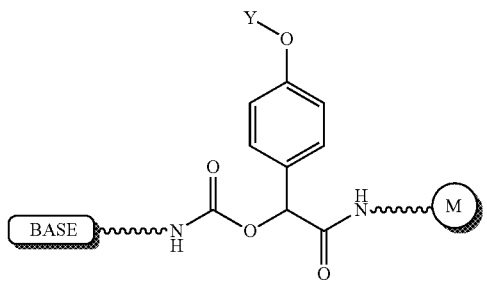

The above shows exemplary embodiment E, where BASE is selected from any ribo- or deoxyribo-nucleobases: adenosine, cytidine, guanosine, thymidine and analogs, M is a detectable marker and Y is a selectively removable protective group.

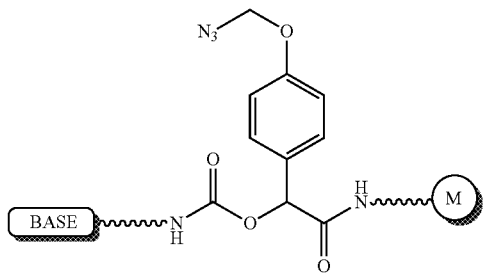

The above shows exemplary embodiment F, where BASE is selected from any ribo- or deoxyribo-nucleobases: adenosine, cytidine, guanosine, thymidine and analogs, M is a detectable marker.

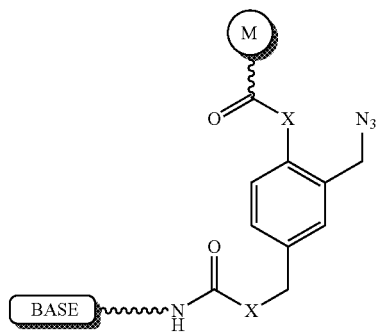

The above shows exemplary embodiment G where BASE is selected from any ribo- or deoxyribo-nucleobases: adenosine, cytidine, guanosine, thymidine and analogs, M is a detectable marker, and X is a divalent group selected from the following: NH, O, S.

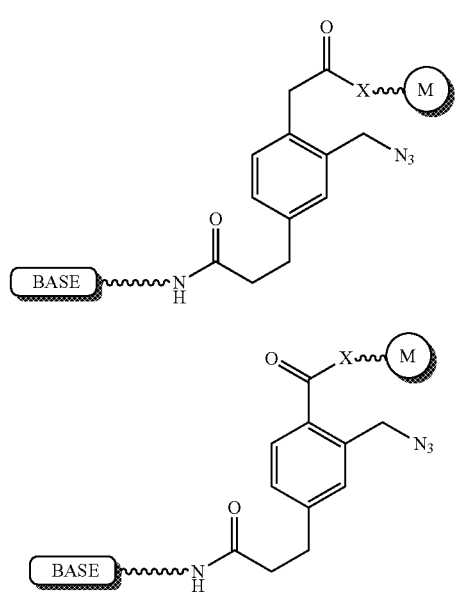

The above shows exemplary embodiment where BASE is selected from any ribo- or deoxyribo-nucleobases: adenosine, cytidine, guanosine, thymidine and analogs, M is a detectable marker, and X is a divalent group selected from the following: NH, O, S. The cleavage is driven here by the reducing agent and nucleophilic attack of the resulting amino group on the carbonyl followed by cyclization. This mechanism has been used before for the development of protective groups for applications in the carbohydrate and nucleoside chemistry (Wada et al. (2001). Tetrahedron Letters 42(6): 1069-1072; Xu et al. (2002) Carbohydrate Research 337(2): 87-91).

The cleavable linker attachment to the base moiety can be achieved in variety of ways that are well known in the art. Among these is the use of linkers based on 1) propargylamino nucleosides, 2) aminoallyl nucleosides, and 3) propargylhydroxy nucleosides.

B. Protective Groups (PG1)

The invention contemplates nucleotide compositions comprising the following blocking or protective groups (PG1) that reside on the 3'-OH groups of the nucleotides: 1) 3'-O-Azidomethyl ethers, 2) 3'-O-disulfide, 3) 3'-O-methylaminoxy, 4) 3'-aminoxy, 5) 3'-oxime and 6) 3'-O-allyl.

With respect to the 3'-O-Azidomethyl ethers, exemplary protective groups that reside on the 3'-OH groups of the nucleotides that are within the scope of this invention are 3'-O-azidomethyl groups. These groups can be removed using mild reducing agents, such as tri(carboethoxy)phosphine (TCEP).

With respect to the 3'-O-disulfide group, the 3'-O-disulfide group can be removed under mild oxidative conditions, for example using in using mild reducing agents, such as .tri(carboethoxy)phosphine (TCEP).

With respect to the 3'-O-methylaminoxy, 3'-aminoxy, and 3'-oxime groups, they can be removed under mild oxidative conditions, for example using in situ generated nitrous acid (such as from sodium nitrite).

As to the 3'-O-allyl group, this protective group can be removed using a variety of reducing agents, including transition metal complexes (Pd, Rh).

Figure 3:
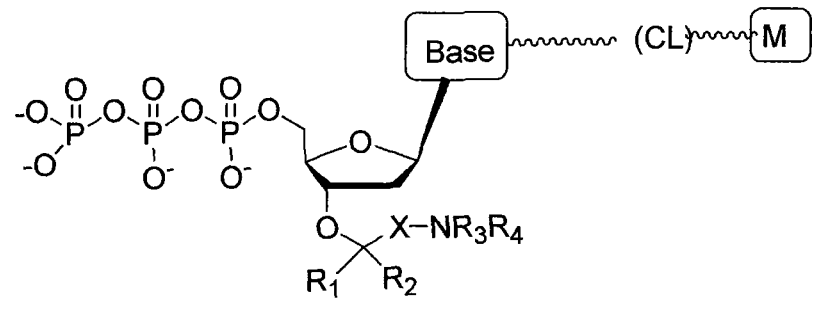
FIG. 3 shows exemplary nucleotide structures with 3'-OH group protection that can be cleaved by mild oxidation reactions.
Figure 3:
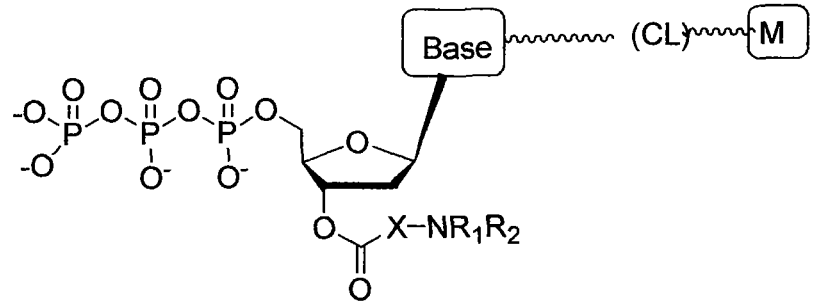

Examples of PG1 protective groups are shown in FIG. 3.

EXPERIMENTAL

The following examples serve to illustrate certain exemplary embodiments and aspects of the present invention and are not to be construed as limiting the scope thereof.

Materials and Methods

The following is a brief description of the exemplary materials and methods used in the following Examples. All solvents and reagents were reagent grades, purchased commercially and used without further purification. Protected nucleosides 5'-O-(tert-butyldimethylsilyl)-2'-deoxythymidine, $N^4$-benzoyl-5'-O-tert-butyldimethylsilyl-2'-deoxycytidine, $N^6$-Benzoyl-5'-O-tert-butyldimethylsilyl-2'-deoxyadenosine, $N^2$-isobutyryl-5'-O-(tert-butyldimethylsilyl)-2'-deoxyguanosine were purchased from CNH Technologies, Inc. All other chemicals were purchased from Sigma-Aldrich.

Example 1

Synthesis of 3'-O-Azidomethyl Nucleotides

The synthesis of 3'-O-azidomethyl-dNPTs is described in FIG. 1. Briefly, reaction of 5'-O-TBDMS-2'-deoxynucleosides (5) with a mixture of DMSO, acetic acid, and acetic anhydride installed the 3'-O-methylthiomethyl group (3'-O-MTM, 6), which upon treatment with $SO_2Cl_2$ converted to activated 3'-O—$CH_2Cl$ (7). The latter can be monitored in TLC as 3'-OH (5) after dissolving in wet organic solvent due to fast hydrolysis of the —$CH_2Cl$ group. The 3'-O—$CH_2Cl$-2'-deoxynucleoside (7) is then treated with $NaN_3$ in dry DMF without purification to convert to 3'-O—$CH_2N_3$ (8). 3'-O-azidomethyl-2'-deoxynucleosides of A, T, and C (9a-9c) were obtained in good yield after deprotection of the 5'-O-TBDMS group as described in the FIG. 1. Similar synthesis route for guanosine (G, 9d), lead only very low yield (>10%) due to formation of a number of side reaction products. To circumvent this, a new method was introduced for the synthesis of guanosine analog (14) which is described in the FIG. 2, which involved protection of the $O^6$— group by diphenylcarbamoyl group. After protection of this particular group, the intermediate (12-14) became less polar, making easier to purify, and lead good overall yield in the azidomethyl group installation step.

Example 2

Synthesis of $N^6$-benzoyl-3'-O-(azidomethyl)-dA (9a)

The following describes exemplary synthesis steps for compounds shown in FIG. 1.

A. Synthesis of $N^6$-Benzoyl-3'-O-(methylthiomethyl)-5'-O-(tert-butyldimethylsilyl)-2'-deoxyadenosine (6a)

3.0 g $N^6$-Benzoyl-5'-O-tert-butyldimethylsilyl-2'-deoxyadenosine (5a) (6.38 mmol) was dissolved in a mixture consisting of 11.96 mL DMSO, 5.46 mL acetic acid, and 17.55 mL acetic anhydride and stirred at room temperature for 48 h. The reaction mixture was then neutralized treating with a sufficient amount of saturated $NaHCO_3$ solution and extracted with CH$_2$Cl$_2$ (3×100 mL). The combined organic extract was then washed with a saturated NaHCO$_3$ solution (100 mL), dried over Na$_2$SO$_4$, and concentrated under vacuum. The resultant yellowish oil was then purified on silica gel column (Hex: EtOAc/1:1 to 1:4) to obtain the product N$^6$-benzoyl-3'-O-(methylthiomethyl)-5'-O-(tert-butyldimethylsilyl)-2'-deoxyadenosine (6a) as white powder in 71% yield (2.4 g, R$_f$ 0.6, EtOAc:hex/7:3). HR-MS: obs. m/z 530.2273, calcd. for C$_{25}$H$_{36}$O$_4$N$_5$SiS 530.2257 [M+H]$^+$. $^1$H-NMR (CDCl$_3$): δ$_H$ 9.00 (s, 1H), 8.83 (s, 1H), 8.35 (s, 1H), 8.05 (d, J=7.6 Hz, 2H), 7.62 (m, 1H), 7.55 (m, 2H), 6.55 (t, J=7.19 Hz, 1H), 4.73 (m, 2H), 4.68 (m, 1H), 4.24 (m, 1H), 3.88 (dd, J=11.19, 3.19 Hz, 1H), 2.74-2.66 (m, 2H), 2.35 (s, 3H), 0.94 (s, 9H) and 0.13 (s, 6H) ppm.

B. Synthesis of N$^6$-benzoyl-3'-O-(azidomethyl)-2'-deoxyadenosine (9a)

To 0.4 g N$^6$-benzoyl-3'-O-(methylthiomethyl)-5'-O-(tert-butyldimethylsilyl)-2'-deoxyadenosine (0.76 mmol) dissolved in 7 mL dry CH$_2$Cl$_2$ was treated with 0.4 mL cyclohexene and 155 µL SO$_2$Cl$_2$ (1.91 mmol) at 0° C. for 2 h. During this time the starting material completely converted to 7a which was shown by disappearance of the starting material and appearance of 3'-OH analog (5a) in TLC (EtOAC:Hex/7:3, R$_f$ 0.3; the 3-CH$_2$Cl (7a) could not detected in TLC due to decomposition in TLC plate to 5a). Then solvent was removed by rotary evaporation and kept about 10 minutes in high vacuum pump. Then dissolved in 5 mL dry DMF and treated with 400 mg NaN$_3$ (6.6 mmol) at room temperature for 3 h. Then the reaction mixture was partitioned in H$_2$O/CH$_2$Cl$_2$, the combined organic part was dried over Na$_2$SO$_4$ and concentrated by rotary evaporation. The crude sample was then dissolved in 5 mL MeOH and treated with 300 mg NH$_4$F (8.1 mmol) more than 38 h. Then MeOH was removed by rotary evaporation. After portioning in H$_2$O/EtOAc, the combined organic part was dried over Na$_2$SO$_4$, concentrated, and purified by silica gel column chromatography (100% EtOAc to 98:2, EtOAc/MeOH) resulting 150 mg of 9a as white powder (48% yield in three steps). HR-MS: Obs. m/z 411.1530, calcd for C$_{18}$H$_{19}$O$_4$N$_8$ 411.1529 [M+H]$^+$. $^1$H-NMR (CDC$_3$): δ$_H$ 8.84 (brs, 1H), 8.70 (brs, 1H), 8.08 (m, 1H), 7.76-7.54 (m, 5H), 6.47 (t, J=5.6 Hz, 1H), 4.83 (m, 2H), 4.78 (m, 1H), 4.39 (m, 1H), 4.09 (d, J=12.78 Hz, H$_5$', 1H), 3.88 (d, J=12.78 Hz, H$_5$", 1H), 3.09 (m, H$_2$', 1H), and 2.65 (m, H$_2$", $^1$H) ppm.

Example 3

Synthesis of 3'-O-azidomethyl-dT (9b)

The following describes exemplary synthesis steps for compounds shown in FIG. 1.

A. Preparation of 3'-O-(methylthiomethyl)-5'-O-(tert-butyldimethylsilyl)-2'-deoxythymidine (6b)

2.0 g 5'-O-(tert-butyldimethylsilyl)-2'-deoxythymidine (5b) (5.6 mmol) was dissolved in a mixture consisting of 10.5 mL DMSO, 4.8 mL acetic acid, and 15.4 mL acetic anhydride and stirred for 48 h at room temperature. The mixture was then quenched by treating with a saturated NaHCO$_3$ solution and extracted with EtOAc (3×100 mL). The combined organic extract was then washed with a saturated solution of NaHCO$_3$ and dried over Na$_2$SO$_4$, concentrated under vacuum, and finally purified by silica gel column chromatography (Hex: EtOAc/7:3 to 1:1). The 3'-O-(methylthiomethyl)-5'-O-(tert-butyldimethylsilyl)-2'-deoxythymidine (6b) was obtained as white powder in 75% yield (1.75 g, R$_f$ 0.6, hex: EtOAc/1:1). HR-MS: Obs. m/z 417.1890, cald. for C$_{18}$H$_{33}$N$_2$O$_5$SSi 417.1879 [M+H]$^+$. $^1$H-NMR (CDCl$_3$): δ$_H$ 8.16 (s, 1H), 7.48 (s, 1H), 6.28 (m, 1H), 4.62 (m, 2H), 4.46 (m, 1H), 4.10 (m, 1H), 3.78-3.90 (m, 2H), 2.39 (m, 1H), 2.14, 2.14 (s, 3H), 1.97 (m, 1H), 1.92 (s, 3H), 0.93 (s, 9H), and 0.13 (s, 3H) ppm.

B. Preparation of 3'-O-(azidomethyl)-2'-deoxythymidine (9b)

To 1.095 g 3'-O-(methylthiomethyl)-5'-O-(tert-butyldimethylsilyl)-2'-deoxythymidine (6b) (2.6 mmol) dissolved in 10 mL dry CH$_2$Cl$_2$ were added 1.33 mL cyclohexene and 284 µL SO$_2$Cl$_2$ (3.5 mmol) at 0° C. and stirred at the ice-cold temperature for 1.5 h. Then the flask temperature was brought to room temperature and transferred to a round bottom flask. The volatiles were removed by rotary evaporation followed by high vacuum pump. Then the crude sample was dissolved in 5 mL dry DMF and 926 mg NaN$_3$ (15.4 mmol) was added to it and stirred for 3 h at room temperature. The crude sample was dispersed in 50 mL distilled water and extracted with CH$_2$Cl$_2$ (3×50 mL), the organic extracts were combined and dried over Na$_2$SO$_4$ and concentrated by rotary evaporation. The crude sample was then dissolved in MeOH (5 mL) and treated with NH$_4$F (600 mg, 16.2 mmol) for 24 h at room temperature. Then reaction mixture was concentrated and partitioned between H$_2$O/CH$_2$Cl$_2$ and the combined organic extract was dried over Na$_2$SO$_4$, concentrated, and purified the product by silica gel column chromatography using Hex: EtOAc/1:1 to 2:5 resulting the final product (9b) as white powders (~550 mg, 71% yield in three steps, R$_f$ 0.3, Hex:EtOAc/1:1.5). HR-MS: Observed m/z 298.1146, calcd for C$_{11}$H$_{16}$O$_5$N$_5$ 298.1151 [M+H]$^+$. $^1$H-NMR (CDC$_3$): δ$_H$ 8.30 (brs, 1H), 7.40 (s, 1H), 6.14 (t, J=6.8 Hz, 1H), 4.79-4.70 (m, 2H), 4.50 (m, 1H), 4.16 (m, 1H), 4.01-3.84 (m, 2H), 2.45 (m, 2H) and 1.95 (s, 3H) ppm.

Example 4

Synthesis of N$^4$-Benzoyl-3'-O-(azidomethyl)-dC (9c)

The following describes exemplary synthesis steps for compounds shown in FIG. 1.

A. Preparation of N$^4$-Benzoyl-3'-O-(methylthiomethyl)-5'-O-(tert-butyldimethylsilyl)-2'-deoxycytidine (6c)

3.5 g N$^4$-benzoyl-5'-O-tert-butyldimethylsilyl-2'-deoxycytidine (5c) (7.65 mmol) was dissolved in a mixture consisting of 14.7 mL DMSO, 6.7 mL acetic acid, and 21.59 mL acetic anhydride and stirred for 48 h at room temperature. During this period of time, a complete conversion to product was observed by TLC(R$_f$=0.4, EtOAc:hex/10:1). The mixture was then neutralized with a saturated NaHCO$_3$ solution and extracted with CH$_2$Cl$_2$ (3×100 mL). The combined organic extract was then washed with saturated solution of NaHCO$_3$ and dried over Na$_2$SO$_4$, and concentrated under vacuum. The product was then purified by silica gel column chromatography (EtOAc:hex/2:1 to 9:1) to obtain N$^4$-benzoyl-3'-O-(methylthiomethyl)-5'-O-(tert-butyldimethylsilyl)-2'-deoxycytidine (6c) as white powder in 73% yield (2.9 g, R$_f$ 0.6, EtOAc:hex/9:1). HR-MS: obs. m/z 506.2134, cald. for C$_{24}$H$_{36}$O$_5$N$_3$SiS [M+H]$^+$. 506.2145. $^1$H-NMR (CDCl$_3$): δ$_H$ 8.43 (d, J=7.1 Hz, 1H), 7.93 (m, 2H), 7.64 (m, 1H), 7.54 (m, 3H), 6.30 (m, 1H), 4.62 & 4.70 (2×d, J=11.59 Hz, 2H), 4.50 (m, 1H), 4.19 (m, 1H), 3.84 & 3.99 (2×dd, J=11.59 & 2.79 Hz, 2H), 2.72 (m, 1H), 2.21 (m, 1H), 2.14 (s, 3H), 0.99 (s, 9H), and 0.16 (s, 6H) ppm.

B. Preparation of N$^4$-Benzoyl-3'-O-(azidomethyl)-2'-deoxycytidine (9c). To 0.5580 g N$^4$-benzoyl-3'-O-(methylthiomethyl)-5'-O-(tert-butyldimethylsilyl)-2'-deoxycytidine (6c) (1.04 mmol) dissolved in 8 mL dry $CH_2Cl_2$ were added 0.56 mL cyclohaxene and 220 µL $SO_2Cl_2$ (2.7 mmol) at 0° C. and stirred at the ice-cold temperature for 1 h. During this time, the starting material converted to the chlorinated product as shown by the 3'-OH (5c) compound in the TLC. The volatiles were then removed under vacuum and resuspended in dry DMF (5 mL) and treated with $NaN_3$ (400 mg, 6.6 mmol) and stirred for 2 h at room temperature. The sample was then partitioned between water and $CH_2Cl_2$ and the organic extracts were combined and dried over $Na_2SO_4$ and concentrated under vacuum. The crude sample was then dissolved in MeOH (5 mL) and treated with $NH_4F$ (600 mg, 16.2 mmol) for 20 h at room temperature. Then solvent was removed under vacuum and extracted with $CH_2Cl_2$ and the organic extract was then dried over $Na_2SO_4$ and concentrated under vacuum. The sample was then purified by silica gel column chromatography (Hex:EtOAc 1:4 to 1:10), and the product (9c) was obtained as white powdery substance (~200 mg, 50% yield in three steps, $R_f$=0.5, EtOAc:Hex/5: 0.5). HR-MS: Obs. m/z 387.1408, calcd for $C_{17}H_{19}O_5N_6$ 387.1417 $[M+H]^+$. $^1$H-NMR ($CDC_3$): $\delta_H$ 8.30 (d, J=7.2 Hz, 1H), 7.93 (d, J=7.50 Hz, 1H), 7.66-7.51 (m, 5H), 6.18 (t, J=6.4 Hz, 1H), 4.81-4.68 (m, 2H), 4.52 (m, 1H), 4.25 (m, 1H), 4.08-3.88 (m, 2H), 2.69 (m, 1H), and 2.50 (m, 2H) ppm.

Example 5

Synthesis of $N^2$-isobutyryl-$O^6$-diphenylcarbamoyl-3'-O-azidomethyl-dG (14)

The following describes exemplary synthesis steps for compounds shown in FIG. 2.

A. Preparation of $N^2$-isobutyryl-3'-O-(methylthiomethyl)-5'-O-(tert-butyldimethylsilyl)-2'-deoxyguanosine (11)

5 g of $N^2$-isobutyryl-5'-O-(tert-butyldimethylsilyl)-2'-deoxyguanosine (11.0 mmol) dissolved in 21 mL dry DMSO was treated with 10 mL acetic acid and 32 mL acetic anhydride, and stirred for 48 h at room temperature. The crude reaction mixture was then neutralized by adding a $K_2CO_3$ solution, and extracted with ethyl acetate (100×3 mL). The combined organic extract was then washed with saturated $NaHCO_3$ solution, dried over $Na_2SO_4$ and concentrated under vacuum. Then reaction mixture was purified by a silica gel column chromatography resulting the product 11 as white powder (3.9 g, 69% yield; $R_f$=0.35, $CH_2Cl_2$:MeOH/ 20:1). HR-MS: Obs. m/z 512.2344 cald. for $C_{22}H_{38}O_5N_5SiS$ 512.2363 $[M+H]^+$. $^1$H-NMR ($CDCl_3$): $\delta_H$ 12.0 (s, 1H), 8.95 (brs, 1H), 8.09 (s, 1H), 6.24 (t, J=6.8 Hz, 1H), 4.73 (m, 2H), 4.66 (m, 1H), 4.16 (m, 1H), 3.81 (m, 2H), 2.76 (m, 1H), 2.59 (m, 1H), 2.54 (m, 1H), 2.21 (s, 3H), 1.29 (m, 6H), 0.91 (s, 9H), and 0.10 (s, 6H) ppm.

B. Synthesis of $N^2$-isobutyryl-$O^6$-diphenylcarbamoyl-3'-O-(methylthiomethyl)-5'-O-(tert-butyldimethylsilyl)-2'-deoxyguanosine (12)

To 1.0 g $N^2$-isobutyryl-3'-O-(methylthimethyl)-5'-O-(tert-butyldimethylsilyl)-2'-deoxyguanosine (11, 1.95 mmol) dissolved in 22 mL dry pyridine were added diphenylcarbamoyl chloride (0.677 g, 2.92 mmol) and 1.02 mL N,N-diisopropylethylamine, and stirred at room temperature for 3 h under nitrogen atmosphere. The reaction mixture became dark red during this time. The solvent was removed under high vacuum, and product was then purified by silica gel column chromatography using EtOAc:hex/1:1 to 7:3 as mobile phase. The product 12 was isolated as yellowish powder (1.09 g, ~80% yield; $R_f$=0.7, EtOAc:hex (1:1)). HR-MS: Obs. m/z 707.3068 calcd. for $C_{35}H_{47}O_6N_6SiS$ 707.3047 $[M+H]^+$. $^1$H-NMR ($CDCl_3$): $\delta_H$ 8.25 (s, 1H), 7.94 (brs, 1H), 7.47-7.37 (m, 10H), 6.42 (m, 1H), 4.75 (m, 2H), 4.71 (m, 1H), 4.18 (m, 1H), 3.88-3.70 (m, 2H), 2.80 (m, 1H), 2.60 (m, 1H), 2.19 (s, 3H), 1.30 (d, J=7.2 Hz, 6H), 0.93 (s, 9H) and 0.14 (s, 6H) ppm.

C. Preparation of $N^2$-isobutyryl-$O^6$-diphenylcarbamoyl-3'-O-azidomethyl-2'-deoxyguanosine (14)

To 786 mg 12 (1.1 mmol) dissolved in 8 mL dry $CH_2Cl_2$ was treated with 0.56 mL cyclohexene and 180 µL $SO_2Cl_2$ (2.2 mmol) at 0° C. and stirred for 1.5 h at the same temperature. The solvent was then removed by rotary evaporation, and further dried under high vacuum for 10 minutes. The crude product was then dissolved in 5 mL dry DMF and reacted with 600 mg $NaN_3$ (10 mmol) at 0° C. and stirred at room temperature for 3 h. Reaction mixture was then partitioned $H_2O/CH_2Cl_2$, the combined organic extract was then dried over $Na_2SO_4$, and concentrated by rotary evaporation. The crude was then dissolved in 5 mL dry MeOH, treated with 500 mg $NH_4F$ (13.5 mmol) at room temperature for more than 24 h. Then MeOH solvent was removed by rotary evaporation, and partitioned ($H_2O/CH_2Cl_2$). The combined organic part was dried over $Na_2SO_4$ and concentrated by rotary evaporation and purified by silica gel column chromatography resulting pure product of 14 as white powder (230 mg, ~36% yield in three steps; hex: EtOAc 1:1 to 1:5, ($R_f$=~0.3, Hex:EtOAc/1:4). HR-MS: Obs. m/z 588.2343, calcd for $C_{28}H_{30}O_6N_9$ 588.2319 $[M+H]^+$. $^1$H-NMR (DFM-$d_6$): $\delta_H$ 8.64 (brs, 1H), 7.48-7.34 (m, 10H), 6.36 (t, J=7.0 Hz), 4.93 (m, 2H), 4.76 (m, 1H), 4.04 (m, 1H), 3.57 (m, 1H), 3.34 (m, 2H), 2.97 (m, 1H), 2.81 (m, 1H), and 1.10 (m, 6H).

Example 6

General Method for the Preparation of 3'-O-Azidomethyl-Dntps

The protected 3'-O-azidomethyl nucleoside (0.3 mmol) and proton sponge (75.8 mg; 0.35 mmol) were dried in a vacuum desiccator over $P_2O_5$ overnight before dissolving in trimethyl phosphate (0.60 mL). Then freshly distilled $POCl_3$ (33 µL, 0.35 mmol) was added drop-wise at 0° C. and the mixture was stirred at 0° C. for 2 h. Subsequently, a well-vortexed mixture of tributylammonium pyrophosphate (552 mg) and tributylamine (0.55 mL; 2.31 mmol) in anhydrous DMF (2.33 mL) was added in one portion at room temperature and stirred for 30 min. Triethyl ammonium bicarbonate solution (TEAB) (0.1 M, 15 mL, pH 8.0) was then added and the mixture was stirred for 1 h at room temperature. Then 15 mL of $NH_4OH$ was added and stirred overnight at room temperature. The resulting mixture was concentrated in vacuo and the residue was diluted with 5 mL of water. The crude mixture was then purified with anion exchange chromatography on DEAE-Sephadex A-25 at 4° C. using a gradient of TEAB (pH 8.0; 0.1-1.0 M). Further purification by RP HPLC to give corresponding target as colorless syrup:

Example 7

3'-O-Azidomethyl Nucleotides Cleavage

The 3'-O-azidomethyl group cleavage can be accomplished with a variety of reducing agents such as phosphines. The cleavage agents that are particularly desirable are those that are soluble in aqueous media and do not cause any damage to the DNA. One particularly desirable agent is tri(carboethoxy)phosphine (TCEP).

The 3'-O-azidomethyl nucleotides can be separated from native nucleotides using RP HPLC. In the next experiment, the kinetics of the 3'-O-azidomethyl TTP cleavage was studied. For this purpose, a 1 mM solution of nucleotide was prepared in water and mixed with 50 mM solution of TCEP/400 mM of Tris at pH 8.0 and incubated at 55 deg C. for various periods of time. After the incubation, the reaction was stopped by mixing with 4 M NaOAc at pH=4.3 and an aliquot of reaction mixture (0.5 nmole of nucleotide) was injected and separated on the RP HPLC column. The integrated peak area was then plotted against time.

We claim:

1. A method for sequencing nucleic acids comprising,
    a) incorporating one or more nucleotides into a plurality of nucleic acids in one or more reaction chambers in contact with one or more charge detectors, wherein said nucleotides comprise a cleavable label and a 3'-OH blocking group,
    b) cleaving said cleavable label under conditions such that a charged moiety is produced, wherein said charged moiety is a positively charged moiety or a negatively charged moiety, the nature of the charge being correlated with the identity of the base; and
    c) detecting said charged moiety with said one or more charge detectors under conditions such that said one or more nucleotides are identified, wherein said positively charged moiety identifies a pyrimidine nucleotide.

2. The method of claim 1, wherein there is a wash step prior to said cleaving which removes unincorporated nucleotides.

3. The method of claim 1, wherein said cleavable label is cleaved enzymatically.

4. The method of claim 1, wherein said cleavable label is cleaved chemically.

5. The method of claim 1, wherein a portion of the sequence of said nucleic acid comprises consecutive identical bases of the formula Xn, where X is any base and n is a whole number between 3 and 10.

6. The method of claim 1, wherein the cleavable label is attached through a cleavable linker to the base of said nucleotide.

7. A method for sequencing nucleic acids comprising,
    a) incorporating one or more nucleotides into a plurality of nucleic acids in one or more reaction chambers in contact with one or more charge detectors, wherein said nucleotides comprise a cleavable label and a 3'-OH blocking group,
    b) cleaving said cleavable label under conditions such that a charged moiety is produced, wherein said charged moiety is a positively charged moiety or a negatively charged moiety, the nature of the charge being correlated with the identity of the base; and
    c) detecting said charged moiety with said one or more charge detectors under conditions such that said one or more nucleotides are identified, wherein said negatively charged moiety identifies a purine nucleotide.

8. The method of claim 7, wherein there is a wash step prior to said cleaving which removes unincorporated nucleotides.

9. The method of claim 7, wherein said cleavable label is cleaved enzymatically.

10. The method of claim 7, wherein said cleavable label is cleaved chemically.

11. The method of claim 7, wherein a portion of the sequence of said nucleic acid comprises consecutive identical bases of the formula Xn, where X is any base and n is a whole number between 3 and 10.

12. The method of claim 7, wherein the cleavable label is attached through a cleavable linker to the base of said nucleotide.

* * * * *